United States Patent
Missfeldt et al.

Patent Number: 5,667,956
Date of Patent: Sep. 16, 1997

[54] SILVER HALIDE RECORDING MATERIAL

[75] Inventors: Michael Missfeldt, Leichlingen; Johannes Willsau, Leverkusen; Ralf Büscher, Lohmar; Peter Bell, Köln; Hans-Ulrich Borst, Elsdorf, all of Germany

[73] Assignee: Agfa, Germany

[21] Appl. No.: 699,466

[22] Filed: Aug. 19, 1996

[30] Foreign Application Priority Data

Aug. 29, 1995 [DE] Germany .......... 195 31 688.6

[51] Int. Cl.$^6$ .......... G03C 1/10; G03C 1/34
[52] U.S. Cl. .......... 430/600; 430/601; 430/610; 430/613; 430/614
[58] Field of Search .......... 430/610, 613, 430/614, 600, 601

[56] References Cited

U.S. PATENT DOCUMENTS

| | | | |
|---|---|---|---|
| 3,271,175 | 9/1966 | Burness et al. | 430/610 |
| 4,668,616 | 5/1987 | Okamura et al. | 430/621 |
| 4,988,615 | 1/1991 | Davies et al. | 430/610 |
| 5,573,900 | 11/1996 | Kawanishi et al. | 430/610 |

FOREIGN PATENT DOCUMENTS

| | | |
|---|---|---|
| 0 304 296 | 2/1989 | European Pat. Off. |
| 1486986 | 6/1967 | France. |
| 90/08978 | 8/1990 | WIPO. |

*Primary Examiner*—Lee C. Wright
*Attorney, Agent, or Firm*—Connolly & Hutz

[57] ABSTRACT

The grain/sensitivity ratio of a photographic silver halide material may be improved by adding a compound of the formula I to one of its layers. The material moreover exhibits a low increase in fog on storage.

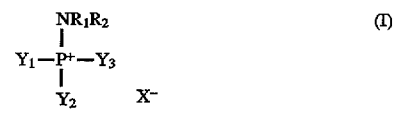

in which:

$Y_1$, $Y_2$, $Y_3$ each mean one of the following residues

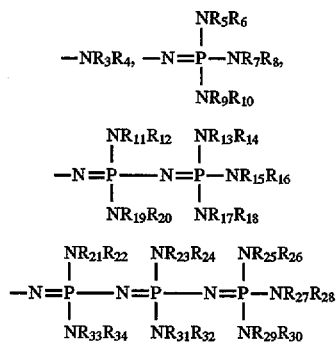

$R_1$ to $R_{34}$ mean H, alkyl or aryl; two residues ($R_1$ to $R_{34}$) located on the same N atom may complete a 5-, 6- or greater-membered ring containing at least one N atom and optionally further heteroatoms; two residues ($R_1$ to $R_{34}$) located on adjacent N atoms may complete a ring involving both N atoms and at least one P atom;

$X^-$ means an anion required to balance the charge, for example $Cl^-$, $Br^-$ or tosylate ($TosO^-$).

6 Claims, No Drawings

SILVER HALIDE RECORDING MATERIAL

This invention relates to a photographic recording material having at least one silver halide emulsion layer and optionally further layers, which material contains a compound of the general formula I in at least one of its layers. The material exhibits improved grain at constant sensitivity and with a lower increase in fog on storage.

As is known, a reduction in grain improves the quality of photographic materials, which improvement is particularly striking in enlargements.

Core/shell emulsions having a certain iodide content in the core are described as grain reducing in WO 91/12 566 and EP-A-0 557 695. An entirely different measure for reducing grain, namely the use of DIP, compounds, is described in EP-A-0 446 863 and EP-A-0 507 092. Certain coupler structures may also have a favourable effect, as is described in EP-A-0 422 595 and EP-A-0 566 115. EP-A-0 377 181 describes the reaction of developer oxidation product (DOP) with certain compounds adhering to the grain as the reason for an improved sensitivity/grain ratio.

Measures taken to influence a specific parameter frequently result in degradation of other photographic properties.

It has been found that grain may be improved by the addition of at least one compound of the general formula I, without degrading sensitivity or any other important photographic property; a reduced increase in fog on storage was also observed.

The present invention provides a photosensitive photographic recording material having at least one photosensitive silver halide layer and optionally further layers, characterised in that it contains a compound of the general formula I in at least one of its layers

in which:

$Y_1$, $Y_2$, $Y_3$ each mean one of the following residues

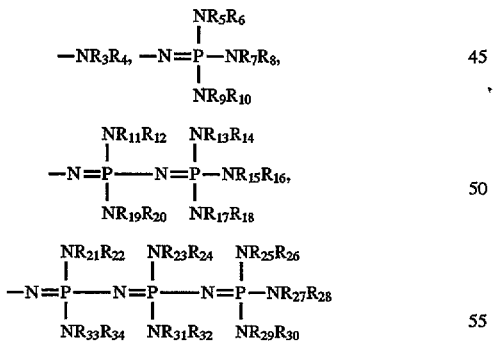

$R_1$ to $R_{34}$ mean H, alkyl or aryl; two residues ($R_1$ to $R_{34}$) located on the same N atom may complete a 5-, 6- or greater-membered ring containing at least one N atom and optionally further heteroatoms; two residues ($R_1$ to $R_{34}$) located on adjacent N atoms may complete a ring involving both N atoms and at least one P atom;

$X^-$ means an anion required to balance the charge, for example $Cl^-$, $Br^-$ or tosylate ($TosO^-$).

The alkyl or aryl residues represented by $R_1$ to $R_{34}$ may optionally be substituted, for example with chlorine. Alkyl residues preferably have up to 6 C atoms; examples are methyl, ethyl, isopropyl, butyl, tertiary butyl ($^tBu$), hexyl. Examples of completed heterocyclic rings are pyrrolidine, piperidine, morpholine, piperazine, 1,3-diaza-2-phosphacyclopentane, 1,3-diaza-2-phosphacyclohexane and 1,3-diaza-2-phosphacycloheptane rings.

Suitable examples of the compounds used according to the invention are shown below:

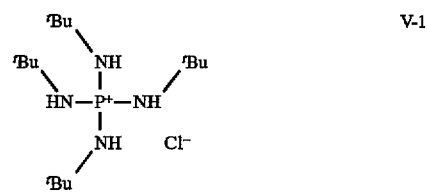

V-1

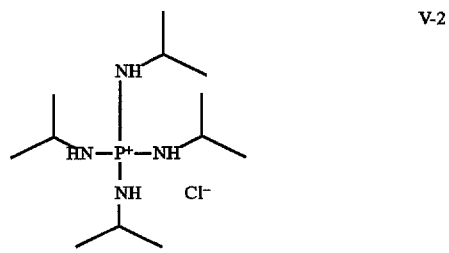

V-2

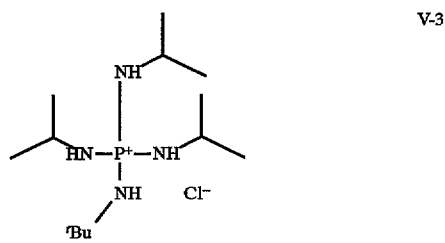

V-3

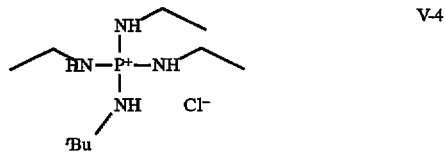

V-4

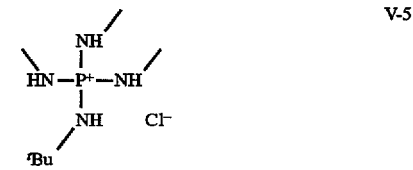

V-5

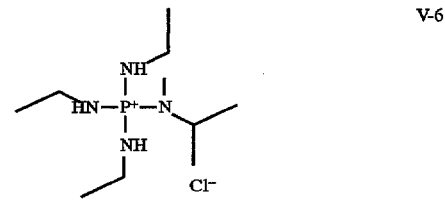

V-6

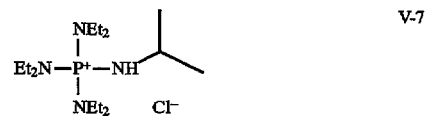

V-7

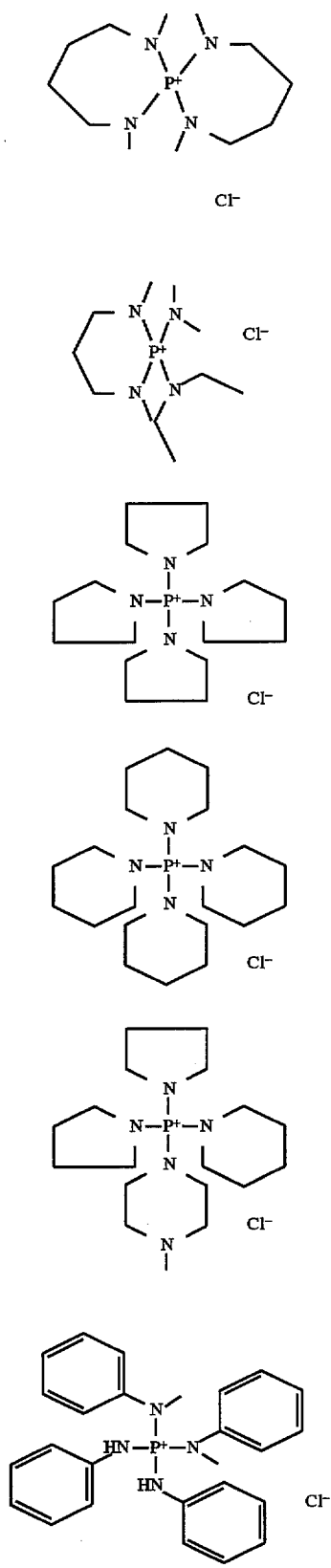

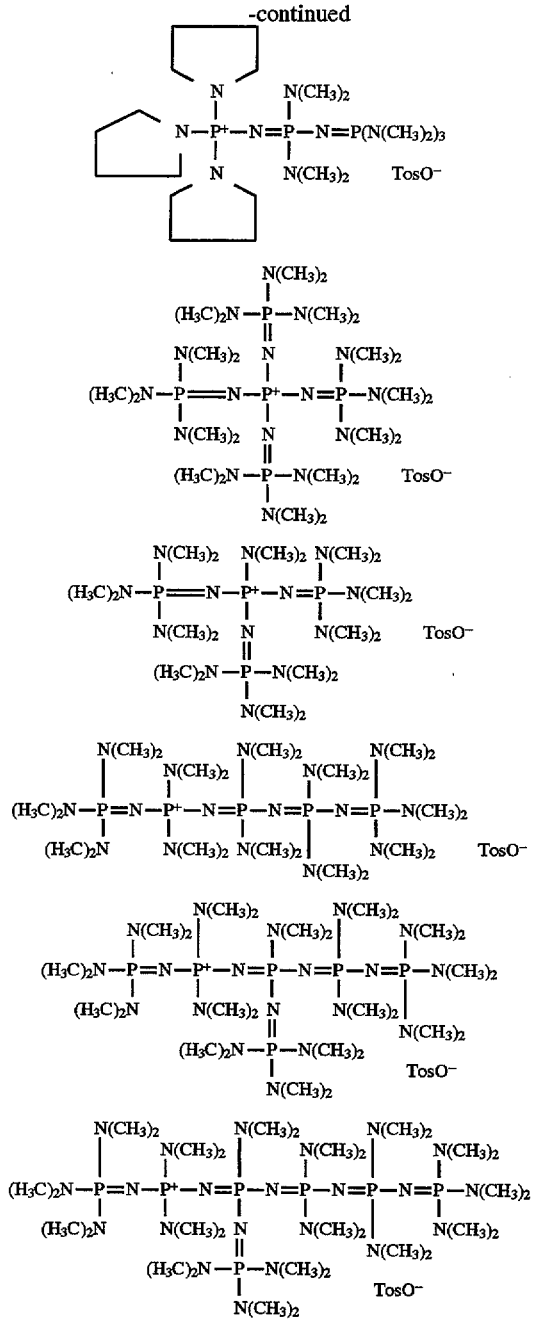

The phosphazene salts containing only one P atom were produced as described in BE 671 026. Phosphazenes with 2 and more P atoms could be synthesised by analogy with the synthetic methods described by R. Schwesinger in *Angew. Chem.*, 103, 1376 (1991) and Angew. Chem., 105, 1420 (1993).

The compounds to be used according to the invention are added to the casting solutions for the layers concerned as an aqueous solution, wherein the compounds may be used individually or as a blend of two or more thereof. They may be added to one or more of the photosensitive layers, namely to a blue-sensitive, a green-sensitive and/or a red-sensitive silver halide emulsion layer or alternatively also to a non-photosensitive binder layer adjacent to one of the above-stated layers. They may advantageously be added both to one of the stated photosensitive silver halide emulsion layers and to a non-photosensitive binder layer adjacent thereto.

The quantity of the added substance is preferably between 1 and 200 mg/m$^2$. The recording material according to the invention has an improved grain/sensitivity ratio, i.e. grain is improved without impairing sensitivity. A lower increase in fog on storage is also observed.

Examples of colour photographic materials are colour negative films, colour reversal films, colour positive films, colour photographic paper, colour reversal photographic paper, colour-sensitive materials for the dye diffusion transfer process or the silver dye bleaching process.

The photographic materials consist of a support onto which at least one photosensitive silver halide emulsion layer is applied. Thin films and sheets are in particular suitable as supports. A review of support materials and the auxiliary layers applied to the front and reverse sides of which is given in *Research Disclosure* 37254, part 1 (1995), page 285.

The colour photographic materials conventionally contain at least one red-sensitive, one green-sensitive and one blue-sensitive silver halide emulsion layer, optionally together with interlayers and protective layers.

Depending upon the type of the photographic material, these layers may be differently arranged. This is demonstrated for the most important products:

Colour photographic films such as colour negative films and colour reversal films have on the support, in the stated sequence, 2 or 3 red-sensitive, cyan-coupling silver halide emulsion layers, 2 or 3 green-sensitive, magenta-coupling silver halide emulsion layers and 2 or 3 blue-sensitive, yellow-coupling silver halide emulsion layers. The layers of identical spectral sensitivity differ with regard to their photographic sensitivity, wherein the less sensitive partial layers are generally arranged closer to the support than the more highly sensitive partial layers.

A yellow filter layer is conventionally located between the green-sensitive and blue-sensitive layers to prevent blue light from reaching the underlying layers.

Colour photographic paper, which is usually substantially less photosensitive than a colour photographic film, conventionally has on the support, in the stated sequence, one blue-sensitive, yellow-coupling silver halide emulsion layer, one green-sensitive, magenta-coupling silver halide emulsion layer and one red-sensitive, cyan-coupling silver halide emulsion layer; the yellow filter layer may be omitted.

The number and arrangement of the photosensitive layers may be varied in order to achieve specific results. For example, all high sensitivity layers may be grouped together in one package of layers and all low sensitivity layers may be grouped together another package of layers in order to increase sensitivity (DE 25 30 645).

Possible options for different layer arrangements and the effects thereof on photographic properties are described in *J. Int. Rec. Mats.*, 1994, volume 22, pages 183–193.

The substantial constituents of the photographic emulsion layers are binder, silver halide grains and colour couplers.

Details of suitable binders may be found in *Research Disclosure* 37254, part 2 (1995), page 286.

Details of suitable silver halide emulsions, the production, ripening, stabilisation and spectral sensitisation thereof, including suitable spectral sensitisers, may be found in *Research Disclosure* 37254, part 3 (1995), page 286 and in *Research Disclosure* 37038, part XV (1995), page 89.

Photographic materials with camera sensitivity conventionally contain silver bromide-iodide emulsions, which may optionally also contain small proportions of silver chloride. Photographic print materials contain either silver chloride-bromide emulsions with up to 80 mol. % of AgBr or silver chloride-bromide emulsions with above 95 mol. % of AgCl.

Details relating to colour couplers may be found in *Research Disclosure* 37254, part 4 (1995), page 288 and in *Research Disclosure* 37038, part II (1995), page 80. The maximum absorption of the dyes formed from the couplers and the developer oxidation product is preferably within the following ranges: yellow coupler 430 to 460 nm, magenta coupler 540 to 560 nm, cyan coupler 630 to 700 nm.

In order to improve sensitivity, grain, sharpness and colour separation in colour photographic films, compounds are frequently used which, on reaction with the developer oxidation product, release photographically active compounds, for example DIR couplers which eliminate a development inhibitor.

Details relating to such compounds, in particular couplers, may be found in *Research Disclosure* 37254, part 5 (1995), page 290 and in *Research Disclosure* 37038, part XIV (1995), page 86.

Colour couplers, which are usually hydrophobic, as well as other hydrophobic constituents of the layers, are conventionally dissolved or dispersed in high-boiling organic solvents. These solutions or dispersions are then emulsified into an aqueous binder solution (conventionally a gelatine solution) and, once the layers have dried, are present as fine droplets (0.05 to 0.8 μm in diameter) in the layers.

Suitable high-boiling organic solvents, methods for the introduction thereof into the layers of a photographic material and further methods for introducing chemical compounds into photographic layers may be found in *Research Disclosure* 37254, part 6 (1995), page 292.

The non-photosensitive interlayers generally located between layers of different spectral sensitivity may contain agents which prevent an undesirable diffusion of developer oxidation products from one photosensitive layer into another photosensitive layer with a different spectral sensitisation.

Suitable compounds (white couplers, scavengers or DOP scavengers) may be found in *Research Disclosure* 37254, part 7 (1995), page 292 and in *Research Disclosure* 37038, part III (1995), page 84.

The photographic material may also contain UV light absorbing compounds, optical whiteners, spacers, filter dyes, formalin scavengers, light stabilisers, antioxidants, $D_{min}$ dyes, additives to improve stabilisation of dyes, couplers and whites and to reduce colour fogging, plasticisers (latices), biocides and others.

Suitable compounds may be found in *Research Disclosure* 37254, part 8 (1995), page 292 and in *Research Disclosure* 37038, parts IV, V, VI, VII, X, XI and XIII (1995), pages 84 et seq.

The layers of colour photographic materials are conventionally hardened, i.e. the binder used, preferably gelatine, is crosslinked by appropriate chemical methods.

Suitable hardener substances may be found in *Research Disclosure* 37254, part 9 (1995), page 294 and in *Research Disclosure* 37038, part XII (1995), page 86.

Once exposed with an image, colour photographic materials are processed using different processes depending upon their nature. Details relating to processing methods and the necessary chemicals are disclosed in *Research Disclosure* 37254, part 10 (1995), page 294 and in *Research Disclosure* 37038, parts XVI to XXIII (1995), pages 95 et seq. together with example materials.

EXAMPLE 1

A colour photographic recording material for colour negative development was produced (layer structure 1A) by applying the following layers in the stated sequence onto a transparent cellulose triacetate layer support. All stated quantities relate to 1 m². The applied quantity of silver halide is stated as the corresponding quantities of $AgNO_3$. All the silver halide emulsions were stabilised with 0.1 g of 4-hydroxy-6-methyl-1,3,3a,7-tetraazaindene per 100 g of $AgNO_3$.

Layer structure

Layer 1:

(Anti-halo layer)

Black colloidal silver sol with 0.3 g of silver 1.2 g of gelatine 0.4 g of UV absorber XUV-1

0.02 g of tricresyl phosphate (TCP)

Layer 2:

(Micrate interlayer)

Micrate silver bromide-iodide emulsion (0.5 mol. % iodide; average grain diameter 0.07 μm) prepared from 0.25 g of $AgNO_3$ with 1.0 g of gelatine Layer 3:

(1st red-sensitised layer, low sensitivity)

Red-sensitised silver bromide-iodide emulsion (4 mol. % iodide; average grain diameter 0.5 μm) prepared from 2.7 g of $AgNO_3$ with 2.0 g of gelatine 0.88 g of cyan coupler XC-1

0.05 g of coloured coupler XCR-1

0.07 g of coloured coupler XCY-1

0.02 g of DIR, coupler XDIR-1

0.75 g of TCP

Layer 4:

(2nd red-sensitised layer, high sensitivity).

Red-sensitised silver bromide-iodide emulsion (12 mol. % iodide; average grain diameter 1.0 μm) prepared from 2.2 g of $AgNO_3$ with 1.8 g of gelatine 0.19 g of cyan coupler XC-2

0.17 g of TCP

Layer 5:

(Interlayer)

0.4 g of gelatine 0.15 g of white coupler XW-1

0.06 g of aluminium salt of aurine tricarboxylic acid

Layer 6:

(1st green-sensitised layer, low sensitivity)

Green-sensitised silver bromide-iodide emulsion (4 mol. % iodide; average grain diameter 0.35 μm) prepared from 1.9 g of $AgNO_3$ with 1.8 g of gelatine 0.54 g of magenta coupler XM-1

0.065 g of coloured coupler XMY-1

0.24 g of DIR coupler XDIR-1

0.6 g of TCP

Layer 7:

(2nd green-sensitised layer, high sensitivity)

Green-sensitised silver bromide-iodide emulsion (9 mol. % iodide; average grain diameter 0.8 μm) prepared from 1.25 g of $AgNO_3$ with 1.25 g of gelatine 0.195 g of magenta coupler XM-2

0.05 g of coloured coupler XMY-2

0.245 g of TCP

Layer 8:

(Yellow filter layer)

Yellow colloidal silver sol with
- 0.09 g of Ag
- 0.25 g of gelatine
- 0.08 g of scavenger XSC-1
- 0.40 g of formaldehyde scavenger XFF-1
- 0.08 g of TCP Layer 9:

(1st blue-sensitive layer, low sensitivity)

Blue-sensitised silver bromide-iodide emulsion (6 mol. % iodide; average grain diameter 0.6 μm) prepared from 0.9 g of AgNO$_3$ with
- 2.2 g of gelatine
- 1.1 g of yellow coupler XY-1
- 0.037 g of DIR coupler XDIR-1
- 1.14 g of TCP Layer 10:

(2nd blue-sensitive layer, high sensitivity)

Blue-sensitised silver bromide-iodide emulsion (10 mol. % iodide; average grain diameter 1.2 μm) prepared from 0.6 g of AgNO$_3$ with
- 0.6 g of gelatine
- 0.2 g of yellow coupler XY-1
- 0.003 g of DIR coupler XDIR-1
- 1.14 g of TCP Layer 11:

(Micrate layer)

Micrate silver bromide-iodide emulsion (0.5 mol. % iodide; average grain diameter 0.06 μm) prepared from 0.06 g of AgNO$_3$, with
- 1.0 g of gelatine
- 0.3 g of UV absorber XUV-2
- 0.3 g of TCP Layer 12:

(Protective and hardening layer)
- 0.25 g of gelatine
- 0.75 g of hardener XH-1 such that, once hardened, the total layer structure had a swelling factor of ≦3.5.

Compounds used in example 1:

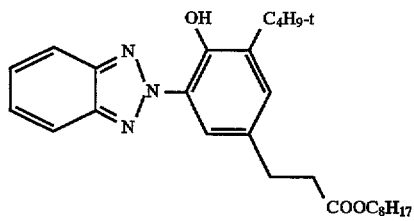

XUV-1

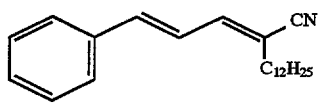

XUV-2

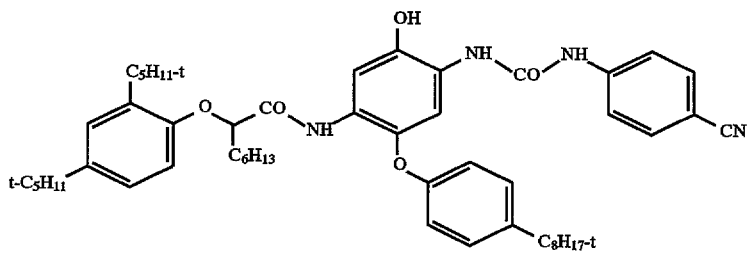

XC-1

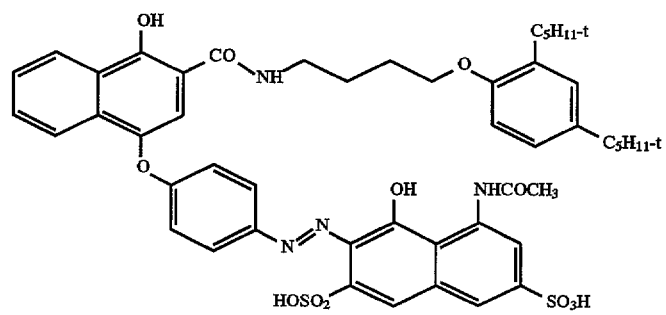

XCR-1

-continued
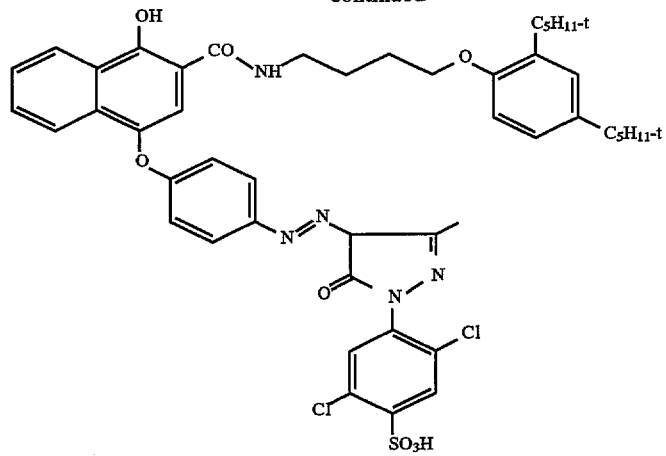
XCY-1
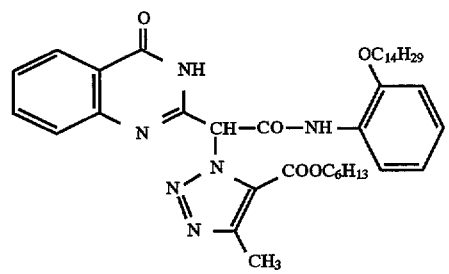
XDIR-1
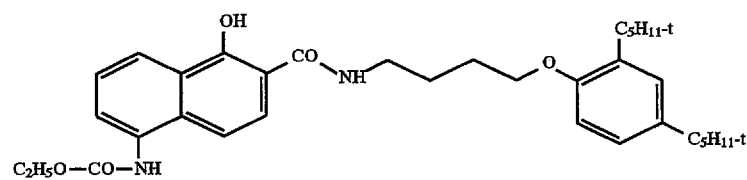
XC-2
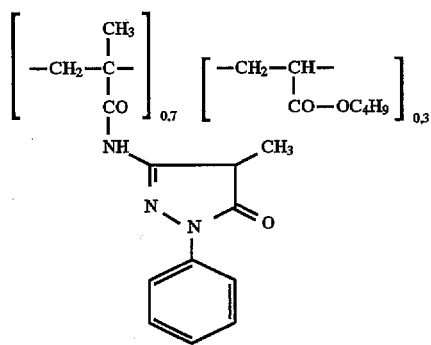
XW-1
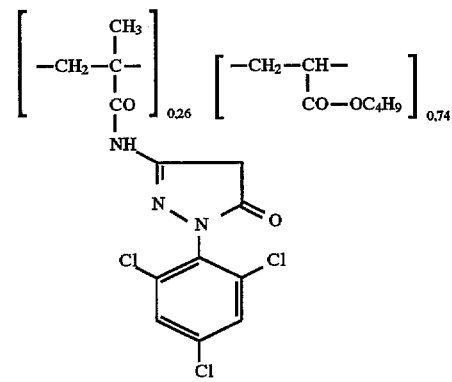
XM-1
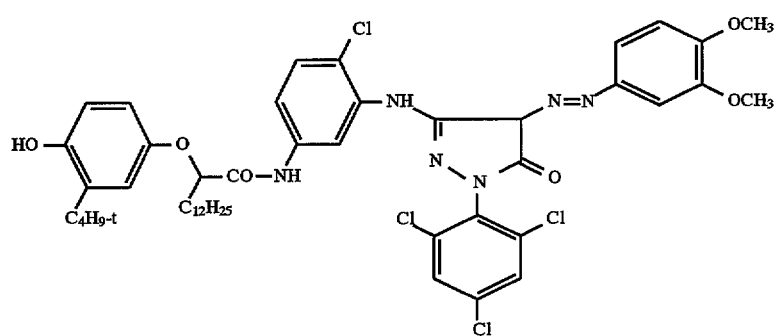
XMY-1

-continued

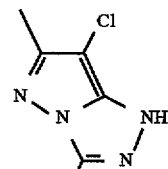
XM-2

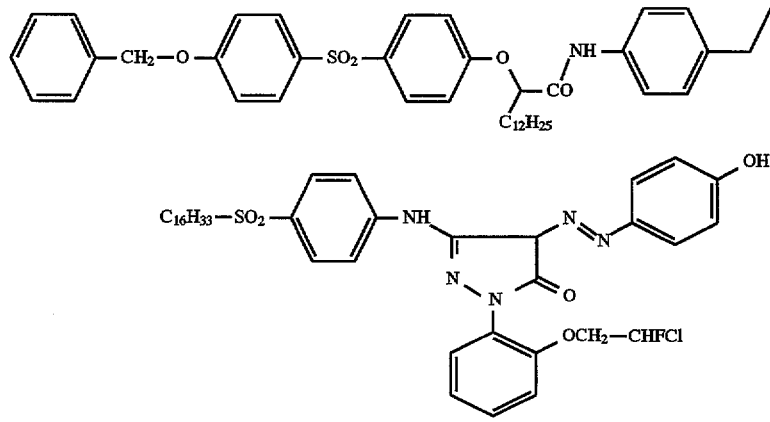
XMY-2

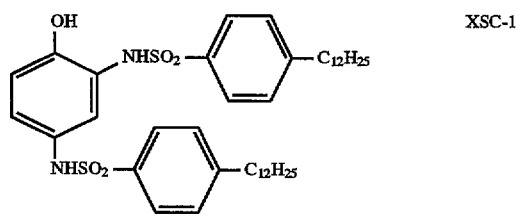
XSC-1

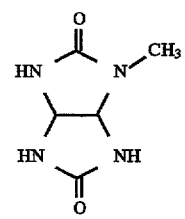
XFF-1

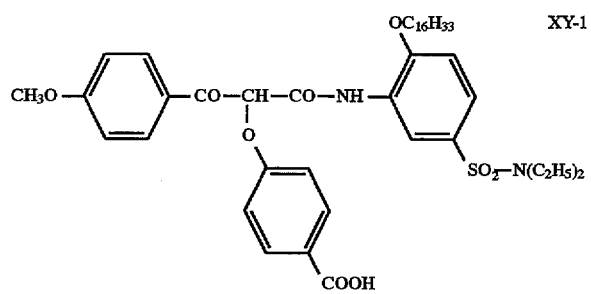
XY-1

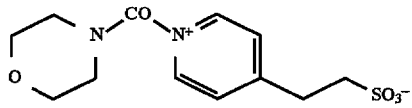
XH-1

After exposure with a grey wedge, development is performed in accordance with *The British Journal of Photography*, 1974, pages 597 and 598.

Layers structures 1B to 1D differ by the addition of a substance according to the invention to the 7th layer. Table 1 summarises the substances used, quantities and results:

TABLE 1

| Material | Substance | Quantity [mg/m$^2$] | Relative green sensitivity | Magenta grain*) | Increase in magenta fog**) | |
|---|---|---|---|---|---|---|
| 1A | — | — | 100 | 12 | 0.10 | Comparison |
| 1B | V-1 | 20 | 99 | 10 | 0.03 | Invention |
| 1C | V-16 | 20 | 102 | 9 | 0.05 | Invention |
| 1D | V-26 | 20 | 102 | 10 | 0.04 | Invention |

*)Grain (RMS) at density 0.6 above fog, values × 1000
**)Increase in fog after two weeks' storage at 60° C. in comparison with material stored at 20° C.

As may be seen, the materials according to the invention exhibit an improvement in grain without degradation of sensitivity. A lower increase in fog on storage is also observed in the materials according to the invention.

EXAMPLE 2

Layer structure 2A differs from layer structure 1A of Example 1 in the composition of the 8th layer.

Layer 8:

(Yellow filter layer)
  0.25 g of gelatine
  0.05 g of yellow dye GF-1
  0.08 g of scavenger SC-1

0.40 g of formaldehyde scavenger XFF-1
0.08 g of TCP

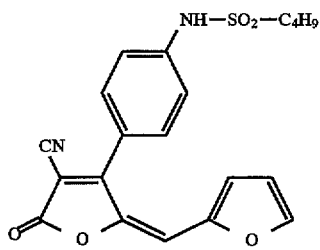

XGF-1

Layer structures 2B to 2D differ by the addition of V-16 to layers 4 or 5. Table 2 summarises the location and quantity of the addition and the results:

TABLE 2

| Material | Layer | Quantity [mg/m²] | Relative red sensitivity | Cyan grain*) | Increase in cyan fog**) | |
|---|---|---|---|---|---|---|
| 2A | — | — | 100 | 13.5 | 0.15 | Comparison |
| 2B | 4 | 29 | 99 | 10.5 | 0.07 | Invention |
| 2C | 5 | 34 | 102 | 11.0 | 0.10 | Invention |

*)Grain (RMS) at density 0.6 above fog, values × 1000
**)Increase in fog after two weeks' storage at 60° C. in comparison with material stored at 20° C.

As may be seen, the materials according to the invention exhibit an improvement in grain without degradation of sensitivity. A lower increase in fog on storage is also observed in the materials according to the invention.

We claim:

1. Photosensitive photographic recording material comprising at least one photosensitive silver halide layer and optionally a further layer or layers, and a compound of the formula I is in at least one of the layers

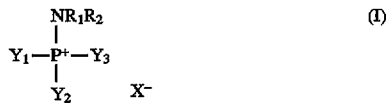

in which:

Y₁, Y₂, Y₃ each mean one of the following residues

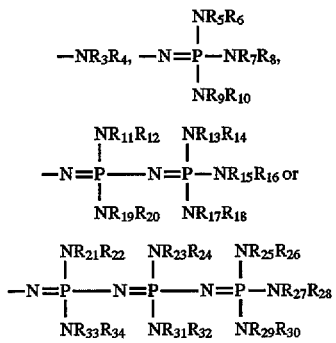

R₁ to R₃₄ are identical or different and mean H, alkyl or aryl; or two residues (R₁ to R₃₄) located on the same N atom may complete a 5-, 6- or greater-membered ring containing at least one N atom and optionally further heteroatoms; or two residues (R₁ to R₃₄) located on two different N atoms may complete a ring involving both N atoms and at least one P atom; and X⁻ means an anion required to balance the charge.

2. Recording material according to claim 1, wherein the recording material contains at least one blue-sensitive silver halide emulsion layer, at least one green-sensitive silver halide emulsion layer and/or at least one red-sensitive silver halide emulsion layer wherein the compound of the formula I is contained in at least one blue-sensitive, one green-sensitive and/or one red-sensitive silver halide emulsion layer.

3. Recording material according to claim 1, wherein the recording material contains at least one blue-sensitive silver halide emulsion layer, at least one green-sensitive silver halide emulsion layer and/or at least one red-sensitive silver halide emulsion layer and said further layer is present and is at least one non-photosensitive binder-layer which is adjacent to a blue-sensitive, green-sensitive or red-sensitive silver halide emulsion layer, and wherein the compound of the formula I is contained in at least one non-photosensitive binder layer.

4. Recording material according to claim 3, wherein the compound of the formula I is contained in at least one blue-sensitive, one green-sensitive and/or one red-sensitive silver halide emulsion layer and in at least one non-photosensitive binder layer adjacent thereto.

5. The recording material according to claim 1, wherein the compound of formula I is selected from the group consisting of

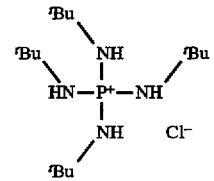

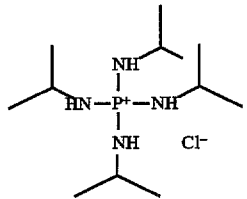

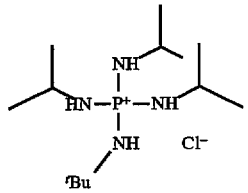

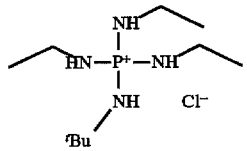

6. The recording material according to claim 1, wherein X⁻ means Cl⁻, Br⁻ or tosylate.

* * * * *